United States Patent [19]

Carson

[11] Patent Number: 5,545,206

[45] Date of Patent: Aug. 13, 1996

[54] LOW PROFILE LEAD WITH AUTOMATIC TINE ACTIVATION

[75] Inventor: Dean F. Carson, Mountain View, Calif.

[73] Assignee: Ventritex, Inc., Sunnyvale, Calif.

[21] Appl. No.: 362,035

[22] Filed: Dec. 22, 1994

[51] Int. Cl.[6] ..................................................... A61N 1/05
[52] U.S. Cl. ........................................ 607/126; 604/265
[58] Field of Search ..................................... 607/120, 122, 607/126–128, 130, 131; 128/642; 604/105–107, 265; 606/198

[56] References Cited

U.S. PATENT DOCUMENTS

| | | |
|---|---|---|
| 3,902,501 | 9/1975 | Citron et al. . |
| 4,409,994 | 10/1983 | Doring ........................ 607/126 |
| 4,458,677 | 7/1984 | McCorkle, Jr. . |
| 4,628,944 | 12/1986 | MacGregor et al. . |
| 4,722,353 | 2/1988 | Sluetz . |
| 4,827,940 | 5/1989 | Mayer et al. .................... 128/642 |
| 4,883,070 | 11/1989 | Hanson ........................... 607/122 |
| 4,913,164 | 4/1990 | Greene et al. . |
| 4,957,118 | 9/1990 | Eriebacher ...................... 607/128 |
| 5,238,007 | 8/1993 | Giele et al. ..................... 607/126 |

FOREIGN PATENT DOCUMENTS 2311807  9/1973  Germany ........................... 604/105

Primary Examiner—William E. Kamm
Assistant Examiner—Jeffrey R. Jastrzab
Attorney, Agent, or Firm—Steven M. Mitchell; M. Elizabeth Bush; Mark J. Meltzer

[57] ABSTRACT

A transvenous lead system for cardiac stimulation with a pacemaker or implantable defibrillator having automatic activation of a passive fixation system. The lead includes an insulative lead body such as silicone rubber and has a proximal end with a connector for coupling the lead to the pacemaker or defibrillator. At least one conductor extends through the lead body for connection to a lead electrode. The lead further includes a plurality of flexible tines. In a first position, the tines are folded back along the lead body and exhibit a minimal profile. A hydrophilic material such as a hydrogel is disposed on the under side of each tine either as part of the tine or between the tine and the lead body. Upon exposure to body fluids when the lead is implanted, the hydrogel absorbs liquid and expands. This expansion forces the tines into a second, deployed position where the tines can engage trabeculae of the heart chambers to anchor the lead in place.

12 Claims, 4 Drawing Sheets

LOW PROFILE LEAD WITH AUTOMATIC TINE ACTIVATION

BACKGROUND OF THE INVENTION

1. Field of the Invention

The present invention relates generally to transvenous cardiac stimulation leads and more particularly to a transvenous lead having a self-actuating fixation mechanism.

2. Prior Art

Transvenously placed cardiac stimulation leads have been used with implantable pacemakers for several decades. More recently, such leads have become the preferred choice for use with implantable cardioverter/defibrillators ("ICDs" or "defibrillators"). Transvenous leads, also called endocardial leads, are typically implanted through an incision in a vein in the area of a patient's collar bone, such as the subclavian vein, and are then guided through the vein to the superior vena cava (SVC) and then to a location in either the right atrium (RA) or through the atrium and the tricuspid valve and into the right ventricle (RV). In several of the different possible applications, the lead requires a fixation mechanism to hold the lead in place, at least until natural fibrotic growth occurs which may then serve to secure the lead in place. A particular example of such a lead is a right ventricular defibrillation lead which typically includes a pacing/sensing tip at the distal end of the lead for positioning in the RV apex and a defibrillation electrode which extends along the lead body starting from a point spaced apart from the distal end to a location approximately where the lead passes through the tricuspid valve.

One problem which must be addressed in designing a transvenous lead is the overall profile or outside diameter of the lead body and its various mechanisms. These may include pacing and defibrillation electrodes, joints used to assemble sections of the lead together and fixation mechanisms. The lead profile is important because any protrusions, particularly sharp ones, or extra large sections may cause trauma to the vein during insertion. The introducer sheath and/or vein incision must be sized to allow the largest diameter of the lead to pass through. It is therefore advantageous to provide a lead having a fairly constant and minimized profile.

A number of different fixation mechanisms have been developed to help secure the lead distal end in the RV apex. Citron et al, U.S. Pat. No. 3,902,501, "Endocardial Electrode", which patent is incorporated herein by reference, discloses an endocardial lead having a plurality of pliant tines which extend from the electrode adjacent the tip and form an acute angle with the electrode body. Various means are disclosed for holding the tines against the lead body during insertion while allowing their release when the tip is in position. The released tines then cooperate with the heart tissue, particularly the trabeculae, to maintain the electrode tip in position. In one embodiment, a hold down shroud is positioned near the lead tip and is adapted to receive at least the ends of the tines and restrain them in position. The tines are released by either inflating a balloon underlying the tines, pulling a line attached to the shroud or stretching the end of the lead by forcing a stylet against the tip. A drawback with each of these designs is that they require additional mechanical complexity which may increase the lead profile and/or increase manufacturing complexity.

In U.S. Pat. No. 4,722,353, to Sluetz, "Stabilizer For Implantable Electrode", tines which extend perpendicularly from the lead body are made sufficiently pliable such that they allegedly do not cause trauma when they are folded back by the vein wall upon insertion of the lead into the vein. It is not clear, however, that this design does not generate any trauma or that it is in fact effective in achieving fixation.

U.S. Pat. No. 4,913,164, "Extensible Passive Fixation Mechanism For Lead Assembly Of An Implantable Cardiac Stimulator" to Greene et al, discloses a fixation mechanism which includes a plurality of tines which are movable from a first unextended position to a second extended position using an essentially umbrella-type actuation mechanism. This system thus includes a significantly complex mechanical actuation for the fixation mechanism which would be difficult to manufacture and which could exhibit reliability problems.

In an alternative design which is referred to as an active fixation mechanism, a helical screw tip is rotationally actuated to screw the tip of a lead into the heart tissue. U.S. Pat. No. 4,827,940, to Mayer et al, "Soluble Covering for Cardiac Pacing Electrode", discloses such a screw tip which has been encased in mannitol to cover the sharp protrusions of the fixation mechanism during insertion of the lead. The mannitol dissolves upon exposure to body fluids and then the tip may be secured in the desired location. This design again requires a somewhat complex mechanical design to achieve fixation.

It is therefore an object of the invention to provide a transvenous lead which has a mechanically simple fixation mechanism.

It is another object of the invention to provide a transvenous lead system with a fixation mechanism having a minimal profile during implantation.

It is a further object of the invention to provide a transvenous lead with a fixation mechanism which is relatively simple to manufacture.

SUMMARY OF THE INVENTION

The present invention provides a transvenous lead system for cardiac stimulation having automatic activation of a passive fixation mechanism. The lead may particularly be used with either a pacemaker or an implantable defibrillator. The lead includes an insulative lead body of a biocompatible material such as silicone rubber or polyurethane. A proximal end of the lead comprises a connector for coupling the lead to the implantable pacemaker or defibrillator. At least one conductor extends through the lead body for connection to a lead electrode. In a pacemaker lead, this may be a distal pacing/sensing tip electrode and in a defibrillator lead it may be a defibrillation electrode and/or a pacing/sensing electrode. The lead further includes a plurality of flexible tines. In a first position, the tines are laid back along the lead body and present a minimal profile. A hydrophilic material such as a hydrogel is disposed on the under side of each tine, incorporated in a portion of the tine facing the lead body or positioned between the tine and the lead body. Upon exposure to body fluids when the lead is implanted in a patient, the hydrogel absorbs liquid and expands. This expansion forces the tines into a second, deployed position where the tines can engage trabeculae of the heart chambers to anchor the lead in place. The hydrogel may be covered by a layer of silicone rubber which includes one or more pores to allow body fluids to reach the hydrogel and expand it. The tines may include a water soluble coating such as mannitol to control the timing of fluid access to the hydrogel.

BRIEF DESCRIPTION OF THE DRAWINGS

The various features and advantages of the present invention may be more readily understood with reference to the following detailed description taken in conjunction with the accompanying drawings in which:

FIGS. 1A and 1B are cross sectional drawings of a distal end of a transvenous lead according to a first embodiment of the invention.

DETAILED DESCRIPTION OF THE INVENTION

Figure 1A:
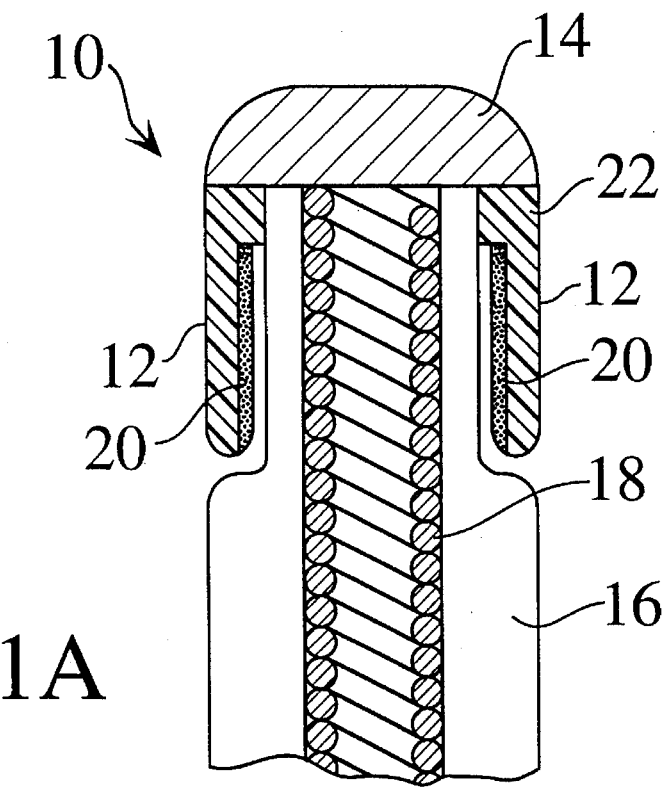
Figure 1B:
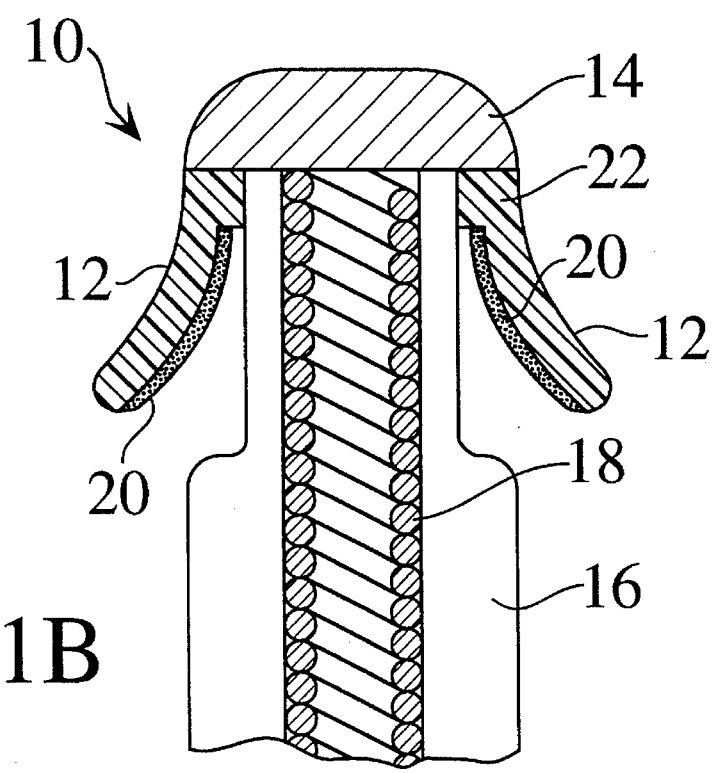

FIGS. 1A and 1B are sectional views of the distal end of a transvenous lead according to a first embodiment of the invention. Each lead 10 has a plurality of tines 12 and an electrically conductive tip 14. The tip 14 may be any conventional pacing tip of a material such as iridium oxide or platinum-iridium. The tines could also be used with a lead which does not include an electrode at its distal tip. A lead body 16 comprises a biocompatible insulative material such as silicone rubber or polyurethane. The tip 14 is electrically coupled to a connector (not shown) at the proximal end of the lead by a coil conductor 18. The connector provides a connection to a pulse generator such as a pacemaker or implantable defibrillator. The tines 12 are constructed principally of the same material as the lead body, i.e. silicone rubber or polyurethane. However, an under side 20 of each tine 12 has a hydrophilic material such as hydrogel attached or incorporated into it. In one embodiment, this is made by molding the hydrogel or a hydrogel/silicone rubber blend onto a sheet of pure silicone rubber. This is then rolled into a hollow cylindrical shape with the hydrogel material on the inside (also referred to as the under side once the tines are molded onto the lead body.) A top end 22 of the cylinder remains pure silicone rubber and does not have the hydrogel incorporated into it in order to facilitate attachment of the cylinder and tines to the lead body. The tines 12 are created by cutting slits into the bottom end of the cylinder. Alternatively, the tines may be shaped by cutting out "fingers" from the side of the sheet which will be the bottom end of the cylinder leaving a plurality of finger-shaped tines with a hydrogel layer 20 on the inside. This cylinder is then slipped over the end of the lead body and molded or glued into place. FIG. 1B shows the tines 12 after they have been exposed to body fluids and the under side or hydrogel layer 20 has absorbed some of the fluid and expanded. The silicone rubber portion of the tines is sufficiently flexible that it is caused to curve away from the lead body by the expansion of the hydrogel layer 20. The cross sectional shape of the tines is not critical, however circular or rectangular shapes are generally preferred.

The hydrogel layer 20 may be pure hydrogel or a blend of silicone rubber and hydrogel as stated above. The mixture is chosen to provide the desired degree of deployment of the tines within a desired time which is on the order of about three to ten minutes after exposure to body fluids. This allows the implanting physician sufficient time to guide the lead through the patient's vein and into the desired position within the heart. The rate of deployment may be further controlled by applying a coating of a soluble material such as mannitol which will dissolve away before the hydrogel begins to hydrate.

Figure 2A:
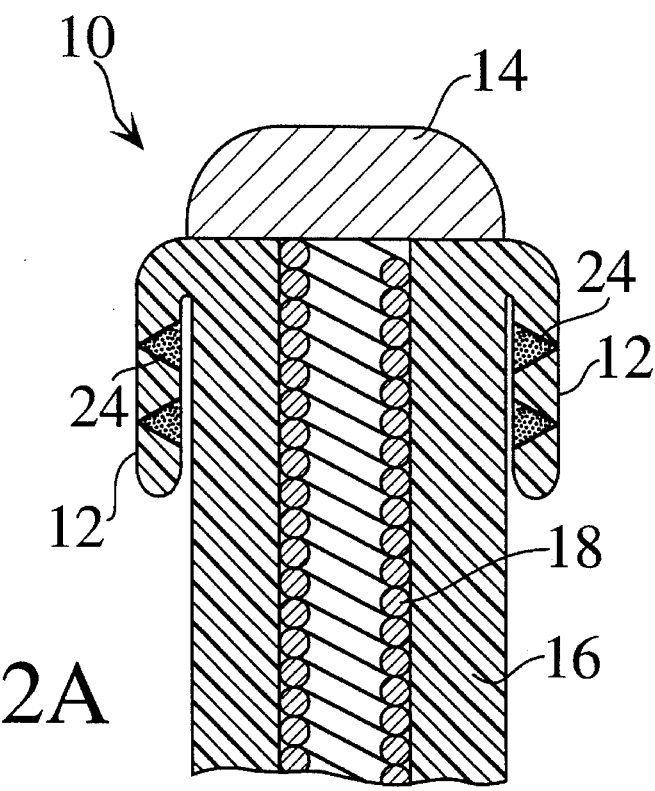
FIGS. 2A and 2B are cross sectional drawings of a distal end of a transvenous lead according to a second embodiment of the invention.
Figure 2B:
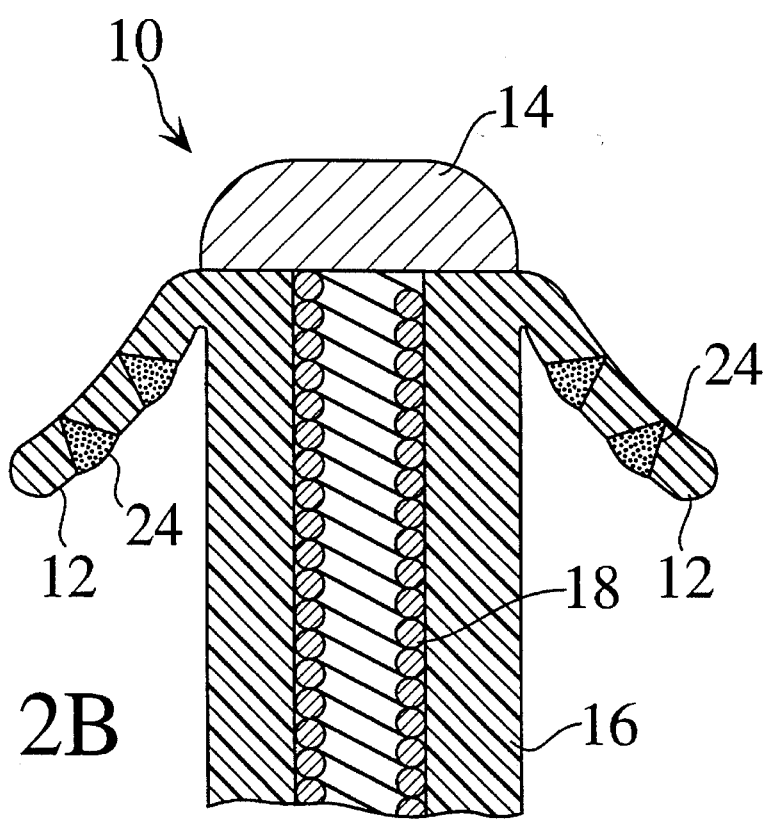

FIGS. 2A and 2B show "before" and "after" cross sectional views of a second embodiment of the invention. Each lead 10 has a plurality of tines 12, an electrically conductive tip 14, a lead body 16, and a coil conductor 18. Each tine 12 includes one or more inserts 24 of hydrogel or a hydrogel/silicone matrix positioned off-center toward the lead body 16 when the tines are in their first position prior to insertion into a patient. As seen in FIG. 2B, when the lead is exposed to body fluids, the tines take on the shape of a segmented curve when the inserts expand, thus causing the tines 12 to deploy into the second position. The inserts 24 could have various shapes as long they are positioned off-center to cause the tines to acquire a curved shape. For example, they can be wedge shaped as shown in FIGS. 2A and 2B. Alternatively, the inserts could be in the form of off-center reservoirs of hydrophilic material spaced along and within the body of the tines. The reservoirs could take the form of small spheres, line segments or other shapes. In that case, poles or other fluid conducting mechanisms are required in the tine material to provide fluid access to the hydrophilic material. Again, a water soluble coating can be used to control the timing of fluid access to the hydrophilic material.

Figure 3A:
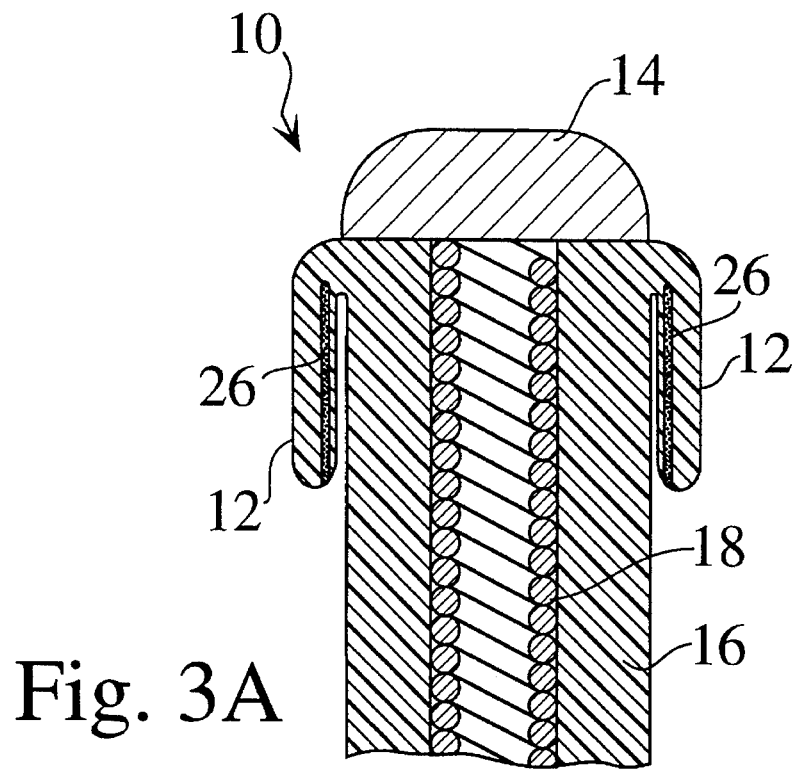
FIGS. 3A and 3B are cross sectional drawings of a distal end of a transvenous lead according to a third embodiment of the invention.
Figure 3B:
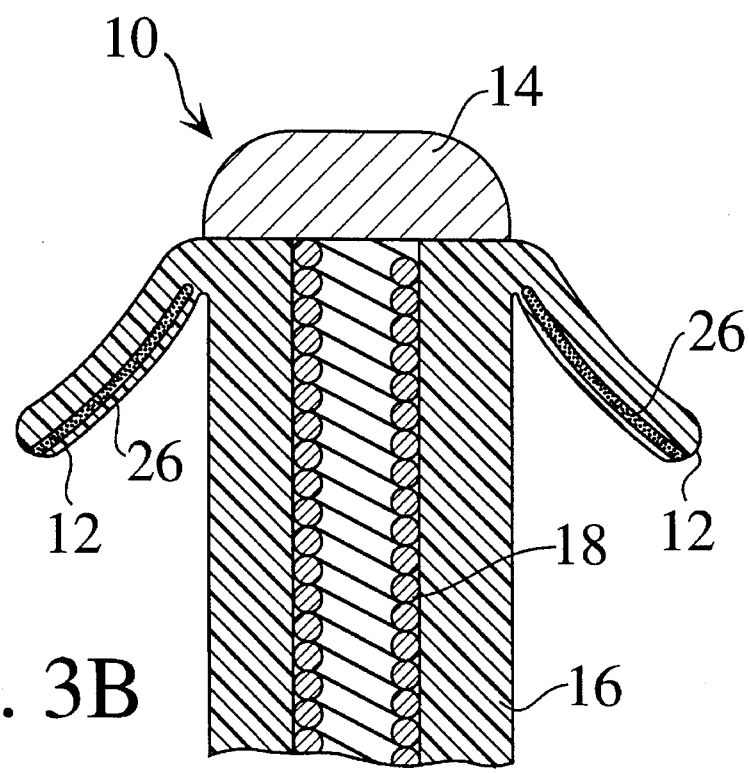

In a third embodiment of the invention, shown in FIGS. 3A and 3B, each of the tines includes an off-center insert 26 of hydrophilic material which runs along substantially the entire length of each tine in the form of an elongated tube. The "tube" could have any desired cross sectional shape such as circular, rectangular or arch shaped. If the water vapor transfer rate of the silicone is not sufficient, the tine material will again require liquid access for the inserts 26 which can be provided by making the tines with a certain amount of porosity, at least in the region of the inserts.

Figure 4A:
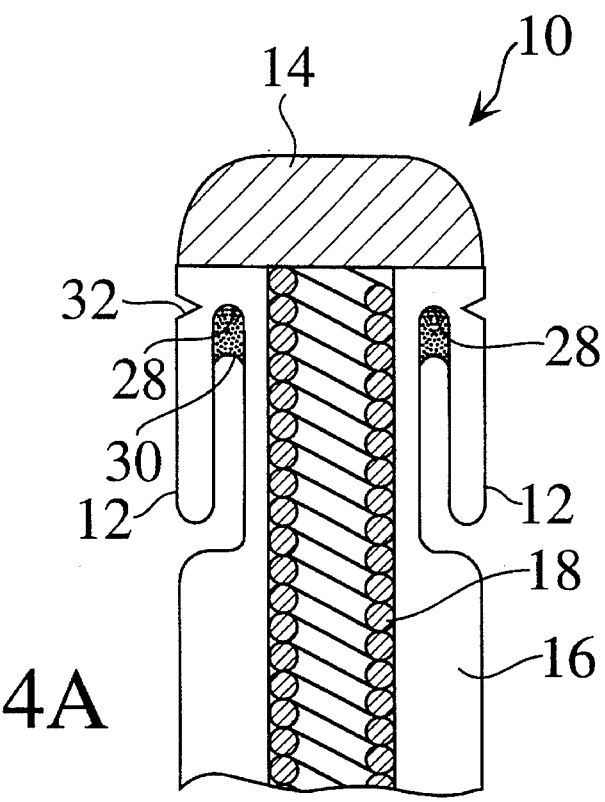
FIGS. 4A and 4B are cross sectional drawings of a distal end of a transvenous lead according to a fourth embodiment of the invention.
Figure 4B:
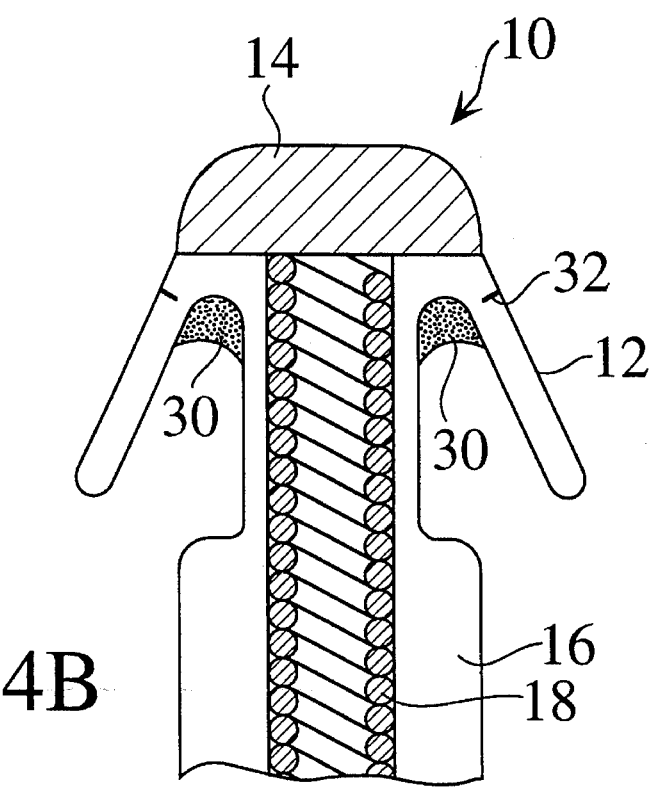

FIGS. 4A and 4B provide cross sectional views of a fourth embodiment of the invention. A pocket 28 is formed under each tine 12 between the tine and the lead body 16. Each pocket 28 is partially filled with a hydrogel 30. When the lead is inserted into a patient, the hydrogel 30 swells forcing the tines away from the lead body. The figures illustrate a configuration where the lead body 16 is necked down in the area under the tines 12 to form the pockets 28. This provides a minimized profile for the lead during insertion. However, the lead need not neck down as radically as shown in the illustration and could be configured so that the lead body diameter does not change in this area. This will be a function of the design requirements for the various electrode, joint and conductor configurations. Additionally, the tines 12 include a notch 32 to provide greater flexibility of a "hinge" structure to reduce resistance of the tines to deployment.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A transvenous cardiac stimulation lead comprising:
   an insulative lead body having proximal and distal ends;
   at least one electrical conductor within said lead body;
   a connector at said proximal end coupled to said conductor for connection to a pulse generator;
   a plurality of flexible tines at said distal end extending substantially parallel to said lead body in a first position and extending away from said lead body in a second position; and a hydrophilic material positioned at an under side of each of said tines;

whereby, when said lead is transvenously implanted with said tines in said first position, after exposure to body fluids said hydrophilic material expands to force said tines to said second position.

2. The lead of claim 1 wherein each of said tines has an axis and said hydrophilic material is positioned within each of said tines and displaced from said axis.

3. The lead of claim 2 wherein said hydrophilic material is blended with a material of said tines and is incorporated into said under side of said tines.

4. The lead of claim 2 wherein said hydrophilic material in each of said tines comprises one or more inserts.

5. The lead of claim 4 wherein said inserts are wedge shaped with a broad side of the wedge facing said lead body when said tines are in said first postion.

6. The lead of claim 2 wherein said hydrophilic material comprises an elongated tube positioned within each of said tines at said under side.

7. The lead of claim 1 wherein each of said tines joins said lead body to form a pocket therebetween and wherein said hydrophilic material is positioned in said pocket.

8. The lead of claim 1 wherein said hydrophilic material is a hydrogel.

9. A fixation mechanism for a transvenous lead comprising:

a longitudinally extending insulative lead body;

a plurality of flexible tines positioned on said lead body and extending substantially parallel to said lead body in a first position and extending away from said lead body in a second position; and a hydrophilic material positioned at an under side of each of said tines;

whereby, when said lead is transvenously implanted with said tines in said first position, after exposure to body fluids said hydrophilic material expands to force said tines to said second position.

10. The lead of claim 9 wherein each of said tines has an axis and said hydrophilic material is positioned within each of said tines and displaced from said axis.

11. The lead of claim 9 wherein said hydrophilic material is blended with a material of said tines and is incorporated into said under side of said tines.

12. The lead of claim 9 wherein said hydrophilic material in each of said tines comprises one or more inserts.

* * * * *